United States Patent
Waldner et al.

(10) Patent No.: US 6,576,192 B1
(45) Date of Patent: Jun. 10, 2003

(54) FLUOROIONOPHORES AND THEIR USE IN OPTICAL ION SENSORS

(75) Inventors: Adrian Waldner, Allschwil (CH); Steven Mark Barnard, San Diego, CA (US); Dirk Beckelmann, Nalbach (DE); David Reinhoudt, Hengelo (NL); Joseph Berger, Muttenz (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/171,333
(22) PCT Filed: Apr. 11, 1997
(86) PCT No.: PCT/EP97/01815
§ 371 (c)(1), (2), (4) Date: Feb. 8, 1999
(87) PCT Pub. No.: WO97/40014
PCT Pub. Date: Oct. 30, 1997

(30) Foreign Application Priority Data

Apr. 18, 1996 (CH) ................................. 979/96

(51) Int. Cl.⁷ .......................... G01N 21/64; G01N 33/20
(52) U.S. Cl. .................... 422/56; 422/57; 422/82.05; 422/82.06; 422/82.07; 422/82.08; 436/73; 436/79; 436/172
(58) Field of Search ................. 436/73, 79, 172; 422/55, 56, 82.05, 82.06, 82.07, 82.08, 57

(56) References Cited

U.S. PATENT DOCUMENTS

| | | | | |
|---|---|---|---|---|
| 4,367,072 A | | 1/1983 | Vögtle et al. ................ 436/501 |
| 4,882,449 A | * | 11/1989 | Harris ......................... 556/419 |
| 5,453,517 A | * | 9/1995 | Kuhn et al. .................. 549/227 |
| 5,464,587 A | * | 11/1995 | Lippitsch et al. ......... 422/82.07 |
| 5,474,743 A | * | 12/1995 | Trend et al. .............. 422/82.07 |
| 5,852,126 A | * | 12/1998 | Barnard et al. .......... 525/326.3 |
| 5,922,612 A | * | 7/1999 | Alder et al. ................ 436/163 |

FOREIGN PATENT DOCUMENTS

| | | | |
|---|---|---|---|
| CA | 2119840 | * | 9/1994 |
| EP | 0623599 | | 11/1994 |
| JP | 5-170707 | * | 7/1993 |
| WO | 89/00997 | | 2/1989 |
| WO | 94/04483 | | 3/1994 |
| WO | 95/01346 | * | 1/1995 |
| WO | 95/29959 | * | 11/1995 |
| WO | 95/30148 | * | 11/1995 |

OTHER PUBLICATIONS

T. Jin et al, J. Chem. Soc., Chem. Commun. 1992, 499–501.*
H. M. Chawla et al, Indian J. Chem. 1993, 32B, 1162–1164, Nov. 1993.*
H. M. Chawla et al, CHem. Abstr. 1995, 123, 111807w, Aug. 1995.*
K. Toth et al, Talanta, 1994, 41, 1041–1049, Jun. 1994.*
K. Iwamoto et al, J. Chem. Soc., Perkin Trans 1 1992, 1885–1887, Aug. 1992.*
H. Chawla et al, J. Indian Inst. Sci. 1994, 74, 515–518, May 1994.*
I. Aoki et al, J. Chem. Soc., Chem. Commun. 1992, 730–732.*
F. Arnaud–Neu et al, J. Chem. Soc., Perkin Trans. 2 1992, 1119–1125.*
M. McCarrick et al, J. Chem. Soc., Chem. Commun. 1992, 1287–1289.*
M. McCarrick et al, Analyst 1993, 118, 1127–1130.*
M. McCarrick et al, J. Chem. Soc., Perkin Trans. 2 1993, 1963–1968.*
D. M. Rudkevich et al, J. Chem. Soc., Perkin Trans. 2 1995, 131–134.*
F. C. J. M. van Veggel et al, Recueil des ravaux Chimiques des Pays–Bas 1995, 114, 387–394.*
F. J. Steemers et al, J. Am. Chem. Soc. 1995, 117, 9408–9414.*
Perez–Jimenez, C. et al., Journal of Materials Chemistry, vol. 4, No. 1, 1994, pp. 145–150.

* cited by examiner

Primary Examiner—Arlen Soderquist
(74) Attorney, Agent, or Firm—Wenderoth, Lind & Ponack, L.L.P.

(57) ABSTRACT

Fluoroionophores of formula (I)

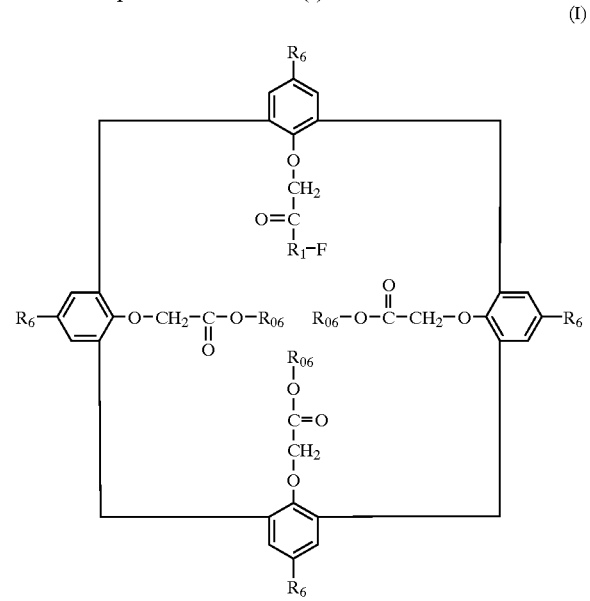

wherein
$R_{06}$ is H or substituted or unsubstituted $C_1$–$C_{20}$alkyl,
$R_6$ is H or substituted or unsubstituted $C_1$–$C_{30}$alkyl or $C_1$–$C_{30}$alkoxy,
$R_1$ is a bridging group, and
F is a residue of a fluorophore.

The fluoroionophores may be covalently bound to support materials and may be used as active components in polymer membranes of optical sensors for the detection of ions. The sensors are distinguished by short response times, a high degree of sensitivity and a long usable life.

35 Claims, No Drawings

FLUOROIONOPHORES AND THEIR USE IN OPTICAL ION SENSORS

This application is a 371 application of PCT/EP97/01815 filed Apr. 11, 19971.

The present invention relates to fluoroionophores containing a fluorophore covalently bound to calix[4]arene via a bridging group and to processes for their preparation. The invention relates also to a) a sensor for determining sodium ions especially in aqueous solutions, which sensor comprises the fluoroionophores in an active layer; b) a method for the qualitative or quantitative determination of sodium ions, especially in aqueous solutions, using the optical sensor; and c) a composition comprising fluoroionophores and polymers.

The optical determination of ions has recently gained greater importance, the presence or concentration of ions being measured, for example, by means of a change in the absorption or fluorescence of a suitable dye. The sensors, also called optrodes, generally consist of a transparent support material and an active layer. The active layer normally comprises a transparent hydrophobic polymer and a lipophilic plasticiser for the purpose of obtaining adequate diffusion of the ions and adequate solubility of the active components. Active components are a specific ionophore as a complexing agent for ions, a counterion for maintaining electrical neutrality, and an indicator substance which, as a result of a chemical change or a physical change in the environment, emits a measurable optical signal. The disadvantages of many such optical sensors are that their response times are too long, they are pH-dependent, their long-term stability is too low for multiple usage and their sensitivities are too low.

The response times may be shortened by covalent linkage of ionophore and fluorophore to form so-called fluoroionophores. Such fluoroionophores are known from WO 89/00997 and U.S. Pat. No. 4,367,072.

In *J. Mater.Chem.* 4(1), (1994), pp. 145–151, Perez-Jimenez et al. describe two novel fluoroionophores that comprise 4 anthracene units covalently bound to calix[4] arene via an amide or ester bond. Disadvantageous fluorescence-quenching effects and lower sensitivity and selectivity as a result of steric hindrance may occur as a result of the close adjacency of the four anthracene units in the molecule.

It has now, surprisingly, been found that calix[4]arenes that comprise only a fluorophore covalently bound already exhibit a high degree of sensitivity and selectivity and are excellently suitable for detecting sodium. It has also, surprisingly, been found that it is possible to bind selectively only a fluorophore covalently to calix[4]arenes, the selectivity of the ionophore being retained. The spacing between the fluorophore and the ionophore can unexpectedly be varied within a wide range by means of the bridging group, without the sensitivity being adversely affected. The ion affinity, which is a necessary precondition for operation as a sensor, is virtually unaltered as a result of the modifications to the calixarene.

The invention accordingly relates firstly to fluoroionophores of formula (I)

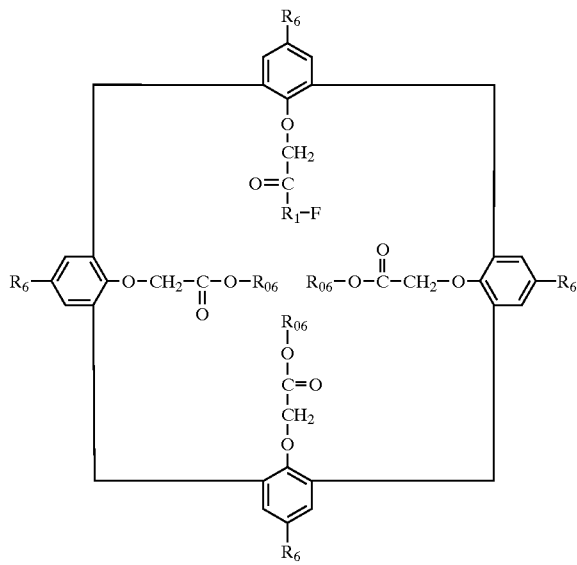

wherein
$R_{06}$ is H or substituted or unsubstituted $C_1$–$C_{20}$alkyl,
$R_6$ is H or substituted or unsubstituted $C_1$–$C_{30}$alkyl or $C_1$–$C_{30}$alkoxy,
$R_1$ is a bridging group, and
F is a residue of a fluorophore.

$R_{06}$ is especially linear or branched $C_1$–$C_{12}$alkyl, more especially linear or branched $C_1$–$C_8$alkyl.

Examples of alkyl are methyl, ethyl and the position isomers of propyl, butyl, pentyl, hexyl, heptyl, octyl, nonyl and decyl.

In a preferred embodiment, $R_{06}$ is H or $C_1$–$C_4$alkyl. More especially $R_{06}$ is tertiary butyl or ethyl.

$R_6$ is especially linear or branched $C_1$–$C_{10}$alkyl, more especially linear or branched $C_1$–$C_4$alkyl.

Examples of alkyl are methyl, ethyl and the position isomers of propyl, butyl, pentyl, hexyl, heptyl, octyl, nonyl and decyl.

In a preferred embodiment, $R_6$ is H or $C_1$–$C_4$alkyl. More especially $R_6$ is tertiary butyl.

The bridging group $R_1$ may contain in the chain from 1 to 30 atoms, preferably from 1 to 20 atoms and especially from 1 to 12 atoms, selected from the group C, O, S and N. The bridging group is preferably a hydrocarbon radical that may be interrupted by one or more hetero atoms from the group O, S and N. For adequate intramolecular interaction between fluorophore and ionophore in the same molecule it may be expedient to select a short bridging group, for example a bridging group having from 1 to 6, preferably from 1 to 4, atoms in the chain.

The bridging group $R_1$ may correspond to formula (II)

wherein $X_1$ is —O— or —NR$_5$,
$X_2$ is a direct bond or is selected from the groups —O—, —S—, —NR$_5$—, —C(O)—O—, —O—C(O)—, —O—C(O)—O—, —SO$_2$—O—, —O—SO$_2$—, —O—SO$_2$—O—, —NR$_5$—C(O)—, —C(O)—NR$_5$—, —NR$_5$—C(O)—O—, —O—C(O)—NR$_5$—, —NR$_5$—C(O)—NR$_5$—, —NR$_5$SO$_2$—, —SO$_2$—NR$_5$—, —NR$_5$—SO$_2$—O—, —O—SO$_2$NR$_5$— and —NR$_5$SO$_2$—NR$_5$—, $R_5$ is H or $C_1$–$C_{30}$alkyl, $C_5$- or $C_6$-cycloalkyl, $C_5$- or $C_6$-cycloalkylmethyl or -ethyl, phenyl, benzyl or 1-phenyleth-2-yl, $R_3$ is a divalent bridging group, r is 0 or 1, with the proviso that r is 1 when $X_2$ is one of the mentioned groups.

When $R_5$ is alkyl it has preferably from 1 to 6 carbon atoms and especially from 1 to 4 carbon atoms. Examples include methyl, ethyl, n-propyl, isopropyl, butyl, hexyl and octyl. When $R_5$ is cycloalkyl it is preferably cyclohexyl, and when $R_5$ is cycloalkylmethyl it is preferably cyclohexylmethyl. In a preferred embodiment, $R_5$ is H or $C_1$–$C_4$alkyl.

The divalent bridging group $R_3$ is preferably a hydrocarbon radical having preferably from 1 to 30 carbon atoms, more preferably from 1 to 18 carbon atoms, especially from 1 to 12 carbon atoms and more especially from 1 to 8 carbon atoms, and is unsubstituted or mono- or poly-substituted by $C_1$–$C_4$alkyl, $C_1$–$C_4$alkoxy or by =O. The hydrocarbon radical may also be interrupted one or more times by hetero atoms selected from the group —O—, —S— and —NR$_5$— wherein $R_5$ is preferably H or $C_1$–$C_4$alkyl.

The divalent bridging group $R_3$ may be, for example, $C_1$–$C_{20}$alkylene, preferably $C_2$–$C_{12}$alkylene, which may be linear or branched. Examples include methylene, ethylene, 1,2- or 1,3-propylene, 1,2-, 1,3- or 1,4-butylene, pentylene, hexylene, octylene, dodecylene, tetradecylene, hexadecylene and octadecylene.

The divalent bridging group $R_3$ may be, for example, polyoxaalkylene having from 2 to 12, especially from 2 to 6, and more especially from 2 to 4, oxaalkylene units and from 2 to 4, preferably 2 or 3, carbon atoms in the alkylene radical. $R_3$ is especially polyoxaethylene or polyoxapropylene having from 2 to 6 oxaalkylene units.

The divalent bridging group $R_3$ may be, for example, $C_5$–$C_{12}$-, especially $C_5$–$C_8$- and more especially $C_5$- or $C_6$-cycloalkyl, such as, for example cyclopentylene, cyclohexylene, cyclooctylene or cyclododecylene.

The divalent bridging group $R_3$ may be, for example, $C_5$–$C_{12}$-, especially $C_5$–$C_8$- and more especially $C_5$- or $C_6$-cycloalkyl-$C_1$–$C_{12}$- or preferably —$C_1$–$C_4$-alkyl. Examples include cyclopentyl-$C_nH_{2n}$— and cyclohexyl-$C_nH_{2n}$—, wherein n is from 1 to 4. -Cyclohexyl-$CH_2$— is especially preferred.

The divalent bridging group $R_3$ may be, for example, $C_5$–$C_{12}$-, especially $C_5$–$C_8$- and more especially $C_5$- or $C_6$-cycloalkyl-($C_1$–$C_{12}$alkyl)$_2$- or preferably $C_1$–$C_4$alkyl)$_2$. Examples include cyclopentyl-($C_nH_{2n}$—)$_2$ and cyclohexyl-($C_nH_{2n}$—)$_2$, wherein n is from 1 to 4. —$CH_2$-Cyclohexyl-$CH_2$— is especially preferred.

The divalent bridging group $R_3$ may be, for example, $C_6$–$C_{14}$arylene, especially $C_6$–$C_{10}$-arylene, for example naphthylene or especially phenylene.

The divalent bridging group $R_3$ may be, for example, $C_7$–$C_{20}$aralkylene, especially $C_7$–$C_{12}$-aralkylene. Arylene-$C_nH_{2n}$— wherein arylene is naphthylene or especially phenylene and n is from 1 to 4 is preferred. Examples are benzylene and phenylethylene.

The divalent bridging group $R_3$ may be, for example, arylene-($C_nH_{2n}$—)$_2$— wherein arylene is preferably naphthylene or especially phenylene and n is from 1 to 4. Examples include xylylene- and phenylene-($CH_2CH_2$)$_2$—.

In a preferred embodiment, the bridging group $R_1$ is preferably —NR$_5$— wherein $R_5$ is H, r is 0 and $X_2$ is a direct bond.

The fluorophores from which F in formula (I) is derived are composed preferably of carbonyl groups, C—C double bonds and aromatic rings, more especially condensed ring systems, such as naphthalenes, anthracenes, benzofurans, benzodiazines, benzotrioxazines, benzotriazepines, pyrenes and coumarins.

The fluorophores from which F in formula (I) is derived may be fluorescein or derivatives thereof, for example fluorescein derivatives of the formulae:

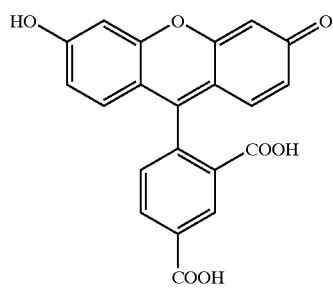

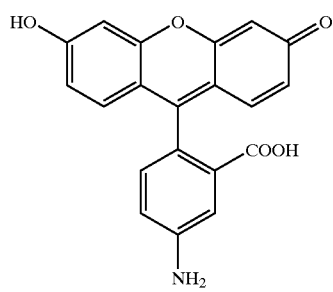

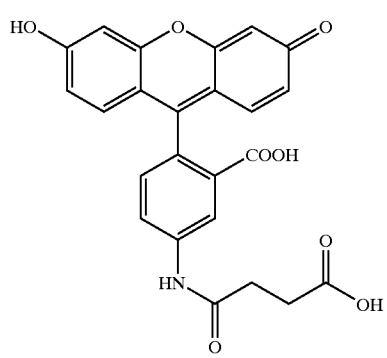

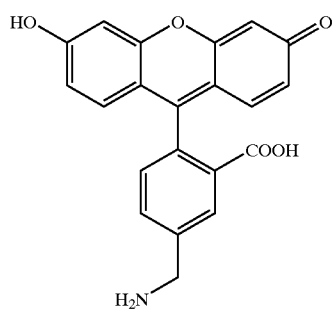

or rhodamines or derivatives thereof, for example of the formulae:

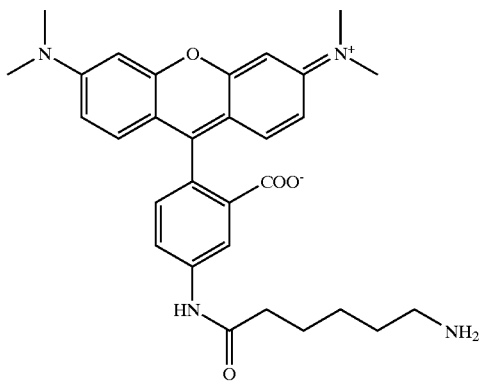

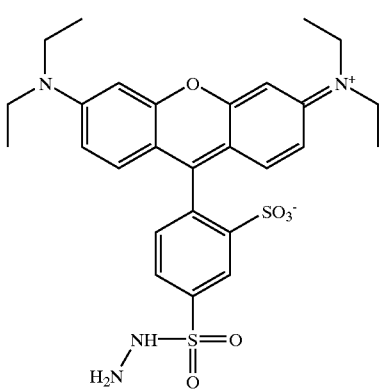

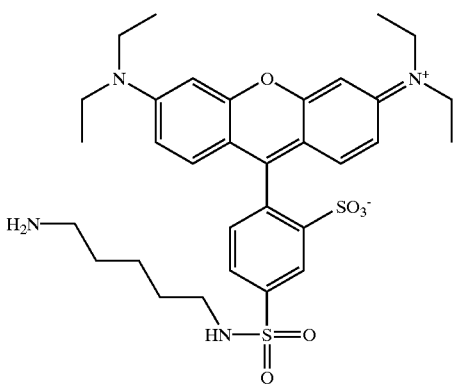

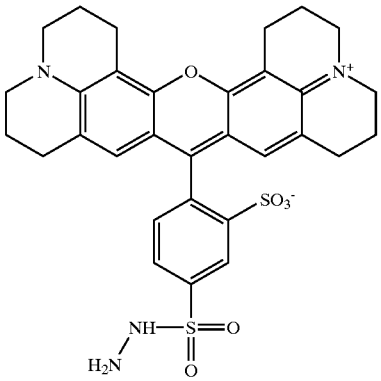

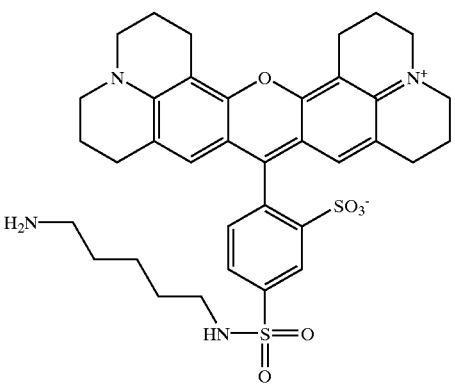

or acridines or derivatives thereof, for example of formula (V):

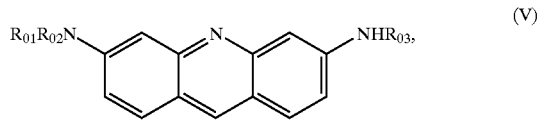

wherein $R_{01}$ and $R_{02}$ are each independently of the other H or linear or branched $C_1$–$C_{30}$-alkyl and $R_{03}$ is H or $C_1$–$C_6$alkyl.

The fluorophore is derived preferably from acridine or rhodamine or derivatives thereof, especially from 3,6-diaminoacridines.

The fluoroionophores to be used according to the invention are preferably compounds of formula (Ia)

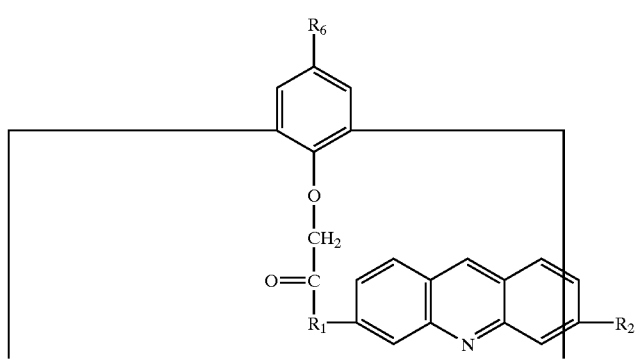

-continued

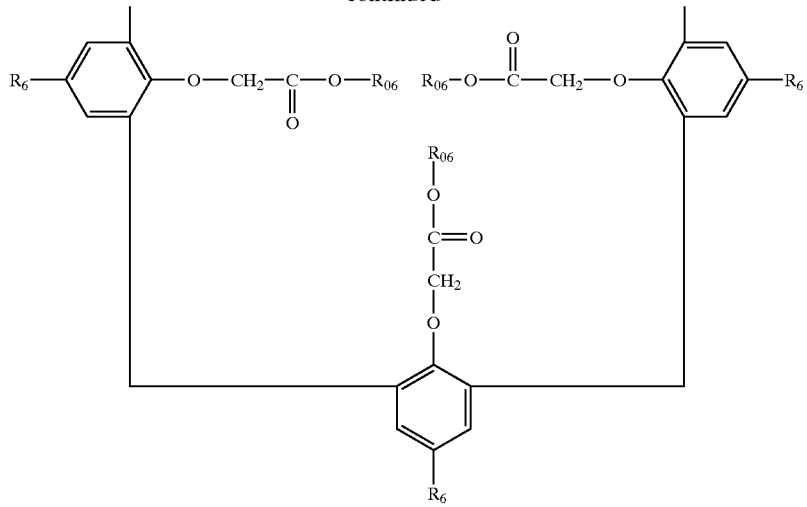

wherein $R_1$, $R_{06}$ and $R_6$ have the meanings and preferred meanings indicated hereinbefore for the compound of formula (I), and $R_2$ is —$NR_{01}R_{02}$ wherein $R_{01}$ and $R_{02}$ are as defined hereinbefore for formula (V), and the minimum carbon atom content is preferably at least 20 carbon atoms.

Especially preferred are fluoroionophores of formula (Ia) in which the bridging group $R_1$ corresponds to formula (II)

wherein $X_1$ is as defined hereinbefore for the compound of formula (II), $X_1$ preferably being NH, and $X_2$ is a direct bond, r is 0 and $R_6$ has the meanings and preferred meanings indicated hereinbefore for the compound of formula (I), and $R_2$ has the meanings and preferred meanings indicated hereinbefore for formula (Ia).

Especially preferred are fluoroionophores of formula (Ia) in which $R_6$ is preferably linear or branched $C_1$–$C_{10}$alkyl, especially linear or branched $C_1$–$C_4$alkyl, more especially tertiary butyl, and $R_1$ has the meanings and preferred meanings indicated hereinbefore for the compound of formula (I) and $R_2$ has the meanings and preferred meanings indicated hereinbefore for the compound of formula (Ia).

Especially preferred are fluoroionophores of formula (Ia) in which $R_{06}$ is preferably linear or branched $C_1$–$C_{10}$alkyl, especially linear or branched $C_1$–$C_4$alkyl, more especially tertiary butyl or ethyl, and $R_1$ has the meanings and preferred meanings indicated hereinbefore for the compound of formula (I) and $R_2$ has the meanings and preferred meanings indicated hereinbefore for the compound of formula (Ia).

Especially preferred are fluoroionophores of formula (Ia) in which $R_2$ is —$NR_{01}R_{02}$ wherein $R_{01}$ and $R_{02}$ are each independently of the other especially H or linear or branched $C_1$–$C_{10}$alkyl, more especially H or linear or branched $C_1$–$C_7$alkyl, and $R_1$ and $R_6$ have the meanings and preferred meanings indicated hereinbefore for the compound of formula (I).

More especially preferred are fluoroionophores of formula (Ia) in which the bridging group $R_1$ corresponds to formula (II)

wherein $X_1$ is as defined hereinbefore for the compound of formula (II), $X_1$ preferably being NH, $X_2$ is a direct bond and r is 0, and wherein $R_6$ is preferably linear or branched $C_1$–$C_{10}$alkyl, especially linear or branched $C_1$–$C_4$alkyl, more especially tertiary butyl, and wherein $R_2$ is —$NR_{01}R_{02}$ wherein $R_{01}$ and $R_{02}$ are each independently of the other especially H or linear or branched $C_1$–$C_{10}$alkyl, more especially H or linear or branched $C_1$–$C_7$alkyl.

There may be mentioned specifically, for example, the following fluoroionophores of the formula

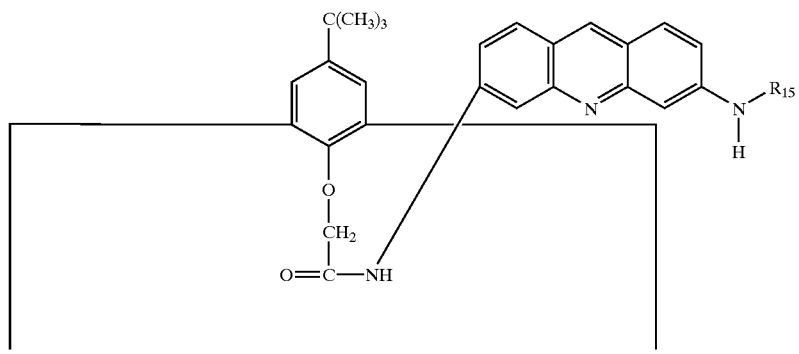

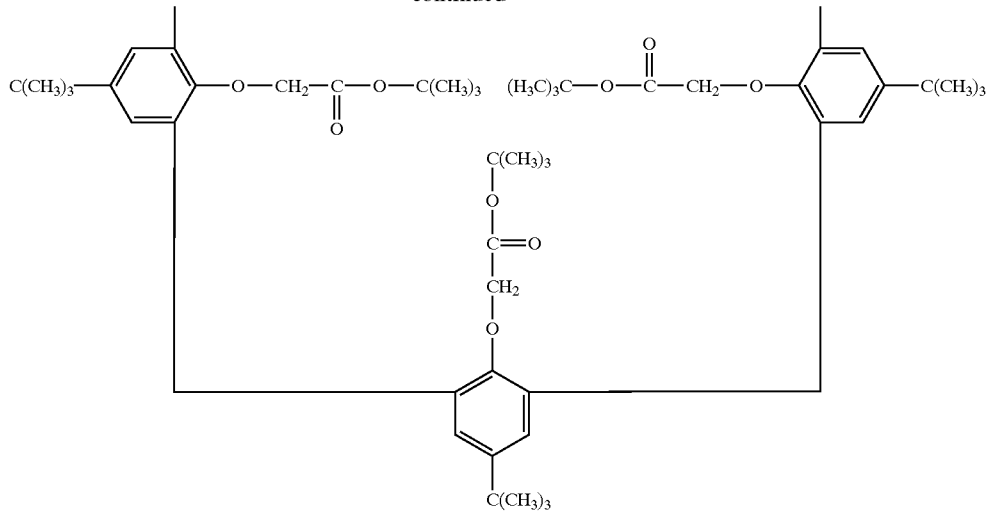
wherein $R_{15}$ is $C_1$–$C_{20}$alkyl, for example methyl, ethyl, propyl, butyl, pentyl, hexyl, heptyl or octyl, and fluoroionophores of the formula
wherein $R_{15}$ is $C_1$–$C_{20}$alkyl, for example methyl, ethyl, propyl, butyl, pentyl, hexyl, heptyl or octyl.
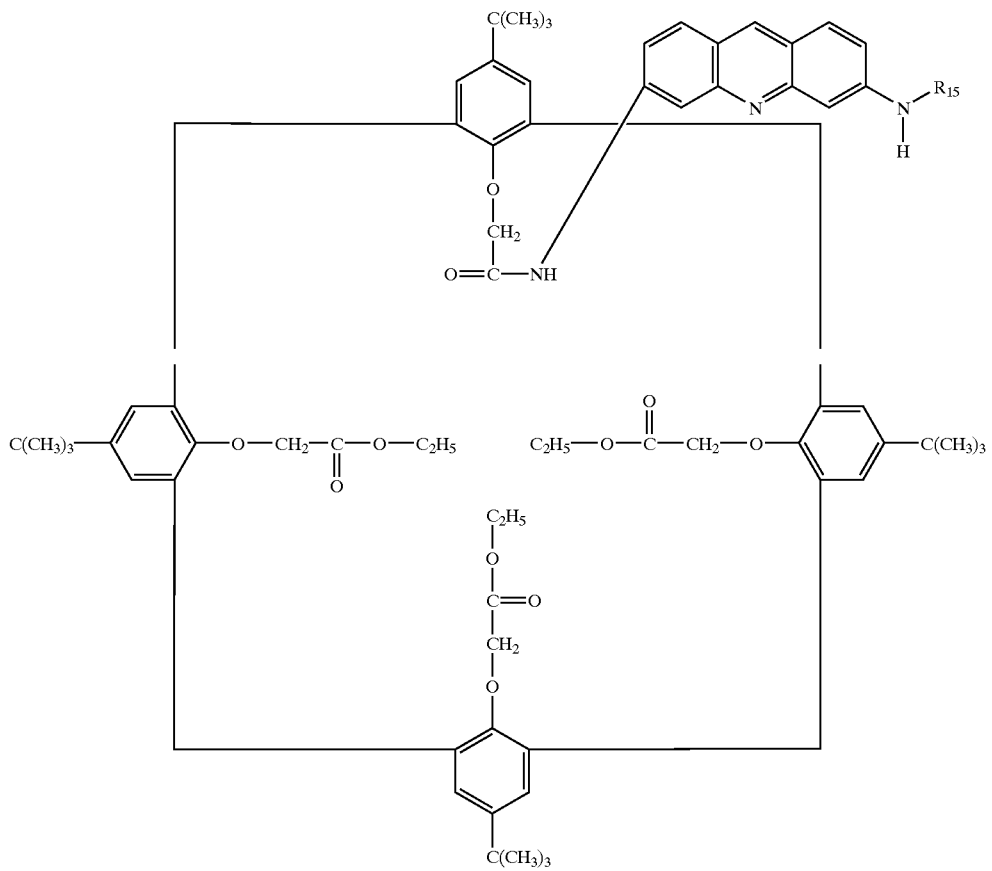

The invention relates also to a process for the preparation of a compound of formula (I) which comprises reacting an ionophore of formula (Ib)

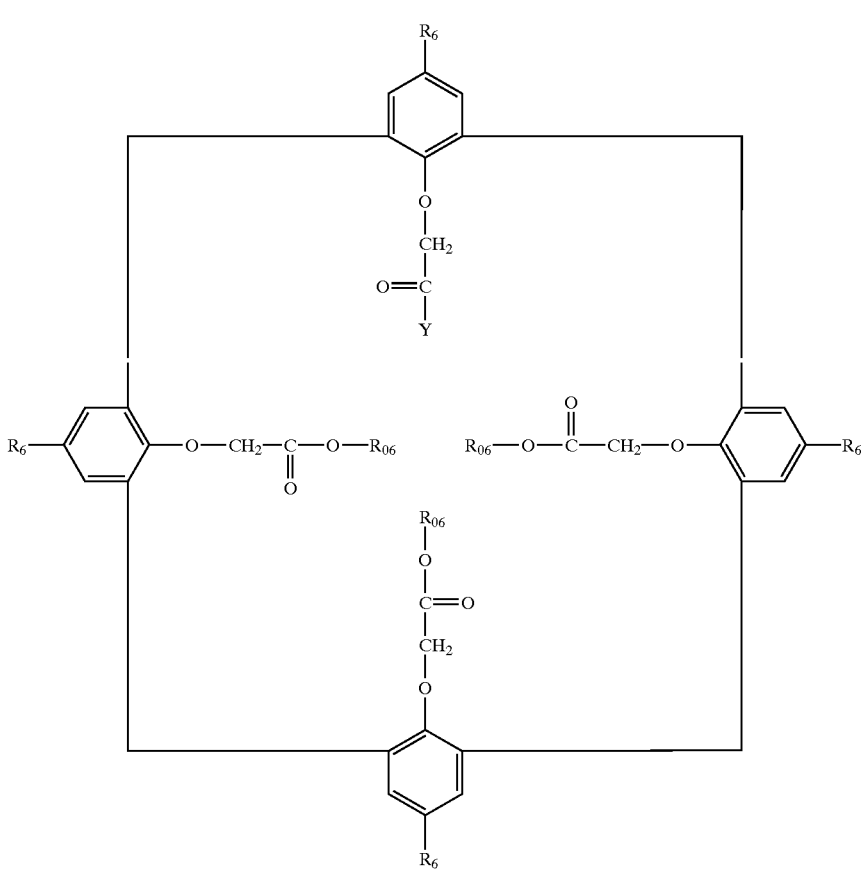

with a fluorophore of formula (Ic)

wherein $R_6$ and $R_{06}$ are as defined hereinbefore for formula (I) and $R_3$ and $X_2$ are as defined hereinbefore for formula (II), and Y in formula (Ib) is Cl or Br and Y' in formula (Ic) is —OH or —$NHR_{03}$ wherein $R_{03}$ is H or $C_1$–$C_6$alkyl.

In order to prepare a compound of formula (I), the functional groups that are not to be reacted may first be protected by protecting groups. The chain can then be extended at that functional group Y'. Known methods are, for example, etherification, esterification, amidation, urea formation and urethane formation.

The compounds of formulae (Ic) and (Ib) are advantageously used in equimolar amounts.

Protecting groups and methods of derivatising functional groups are known from organic chemistry textbooks (E. Breitmaier, Günther Jung; Organische Chemie II (1983); Georg Thieme Verlag Stuttgart, New York p. 342, 409ff).

The functional groups may be protected, for example, by derivatisation. Functional groups of the —XH type (X=O, S, NH) may be protected by acylation; acyl derivatives or carbonic acid derivatives may thus be prepared. Carboxy-protecting groups are known from peptide synthesis, for example methyl or ethyl, dimethylethylene or ptoluene-sulfonic acid. Protecting groups for amino functions may be, for example, benzyloxycarbonyl, tert-butyloxycarbonyl, ptoluenesulfonyl, 2-nitrophenylsulfenyl, trifluoroacetyl or fluorenyl-methoxycarbonyl.

The linkage via functional groups may be carried out in accordance with generally known methods. It is, in principle, also possible to convert any functional groups that are present into different functional groups, for example to convert —$CH_2OH$ groups by oxidation into carboxylic acids, carboxylic acids into amides or halides, amine groups into isocyanate groups, and alcohols or amines into carbonates or urethanes. It is also possible for alcohols or amines to be reacted first of all with halocarboxylic acids (for example chloroacetic acid). Chain-extenders, for example epoxides, azirine, diols, diamines, dicarboxylic acids or esters and diisocyanates, may also be employed one or more times in succession, thus determining the length of the bridging group in a defined manner. Those linkage methods and procedures are known and are described in the specialist literature.

The reactions may be carried out with customary inert organic solvents at temperatures of from 0° C. to 200° C.

Suitable inert solvents are, for example, aprotic solvents, which may be used alone or in the form of mixtures of at least two solvents. Examples are: ethers (dibutyl ether, tetrahydro-furan, dioxane, ethylene glycol monomethyl or dimethyl ether, ethylene glycol monoethyl or diethyl ether, diethylene glycol diethyl ether, triethylene glycol dimethyl ether), halogenated hydrocarbons (methylene chloride, chloroform, 1,2-dichloroethane, 1,1,1-trichloroethane, 1,1, 2,2-tetrachloroethane), carboxylic acid esters and lactones (ethyl acetate, methyl propionate, ethyl benzoate, 2-methoxyethyl acetate, γ-butyrolactone, δ-valerolactone, pivalo-lactone), carboxylic acid amides and lactams (N,N-dimethylformamide, N,N-diethylform-amide, N,N-dimethylacetamide, tetramethylurea, hexamethylphosphoric acid triamide, γ-butyrolactam, ε-caprolactam, N-methylpyrrolidone, N-acetylpyrrolidone, N-methylcapro-lactam), sulfoxides (dimethyl sultoxide), sulfones (dimethylsulfone, diethylsulfone, tri-methylenesultone, tetramethylenesulfone), tertiary amines (N-methylpiperidine, N-methyl-morpholine), aliphatic and aromatic hydrocarbons, for example petroleum ether, pentane, hexane, cyclohexane, methylcyclohexane, benzene or substituted benzenes (chloro-benzene, o-dichlorobenzene, 1,2,4-trichlorobenzene, nitrobenzene, toluene, xylene) and nitriles (acetonitrile, propionitrile, benzonitrile, phenylacetonitrile).

The compounds of formula (I) may be isolated in customary manner by precipitation, crystallisation, distillation or extraction and, where appropriate, may be purified by means of recrystallisation or chromatography.

The acids formed in the reaction are advantageously bound with hydrogen halide acceptors, for example with alkali metal carbonates or with tertiary amines, especially with sterically hindered tertiary amines.

Further details of the preparation of a compound of formula (I) will be found in the Examples.

The fluoroionophores according to the invention are excellently suitable as active components in optical ion sensors for the detection of sodium ions by means of a change in fluorescence.

The invention relates also to a composition comprising fluoroionophores according to the invention and polymers.

Various hydrophilic and hydrophobic polymers are suitable for the composition, "hydrophobic" indicating that the water content in the polymers is a maximum of 15% by weight, preferably a maximum of 10% by weight, especially a maximum of 5% by weight, and more especially a maximum of 3% by weight, based on the polymer. Advantageously the polymers have a mean molecular weight of at least 5,000, especially at least 10,000 and more especially at least 20,000 daltons, for example from 20,000 to 200,000 daltons, especially from 50,000 to 4 million daltons. The polymers must be sufficiently soluble in organic solvents for them to be mixed with the other components and for them to be processed to form layers using customary coating methods. In addition, the polymers must be permeable to ions. The glass transition temperature is preferably from −1300 to 300° C. The dielectric constant of the polymers at 100 Hz and room temperature is especially from 2 to 50, more especially from 5 to 15. The optical transparency is especially in the range from 350 to 1200 nm, more especially from 400 to 900 nm.

Suitable polymers are known to the person skilled in the art and may be homo- or copolymers, block polymers, graft polymers or polymer blends. The polymer blends may be composed of, for example, polymer components having high and low glass transition temperatures. The glass transition temperature can be adjusted, for example, by the polarity, chain length and content of the structural units. The polymers may be selected, for example, from the group of polyvinyl compounds and polyacrylates, polyesters, polyamides, polyethers, polyimides, polyester amides, polyamide imides, polyurethanes, polyether urethanes, polyester urethanes, polyureas, polyurethane ureas and polysiloxanes, it being possible for the polymers to contain ionisable basic groups (for example amino groups) or acidic groups (for example carboxylic or sulfonic acid groups), which may help to provide improved ion transport.

Examples of monomers for polyolefin preparation include acrylic acid, methacrylic acid, maleic acid, maleic acid anhydride, acrylic and methacrylic acid $C_1$–$C_{30}$esters, acrylic and methacrylic acid $C_1$–$C_{30}$amides or acrylic and methacrylic acid amide, vinyl esters of $C_1$–$C_{20}$carboxylic acids, acrylonitrile, styrene, α-methylstyrene, vinyl chloride, vinyl fluoride, vinylidene chloride, vinyl ethers of $C_1$–$C_{30}$alcohols and polyurethanes.

Polyesters, polyester amides and polyamides are composed especially of $C_2$–$C_{12}$-di-carboxylic acids and $C_2$–$C_{18}$-diols or -diamines. Polyimides are composed especially of $C_2$–$C_{18}$tetracarboxylic acids and $C_2$–$C_{18}$diamines. Polyethers are composed especially of aliphatic $C_2$–$C_{12}$diols (1,2- or α,ω-linkage) or linear adducts of such diols and $C_8$–$C_{30}$diglycidyl ethers. Polyurethanes and polyureas are composed especially of $C_2$–$C_{18}$-diols or -diamines and $C_2$–$C_{20}$-diisocyanates and/or -triisocyanates. Polysiloxanes are composed especially of di-$C_1$–$C_4$alkylsilyidichlorosilanes.

In a preferred embodiment, the polymers are polyurethanes of polyethers of $C_3$–$C_6$-alkanediols and aliphatic, cycloaliphatic, cycloaliphatic-aliphatic, aromatic-aliphatic or aromatic $C_2$–$C_{20}$diisocyanates, for example of polytetrahydroturan and bis(p-diiso-cyanatocyclohexyl)methane (Tecoflex).

In another preferred embodiment, the polymers are copolymers containing from 10 to 90 mol %, especially from 20 to 80 mol %, more especially from 30 to 70 mol %, of identical or different structural units of formula III

and from 90 to 10 mol %, especially from 80 to 20 mol %, more especially from 70 to 30 mol %, based on the polymer, of identical or different structural units of formula IV

wherein $R_7$ and $R_8$ are each independently of the other H or $C_1$–$C_4$alkyl, X is —O— or —$NR_{14}$—,
$R_9$ is $C_6$–$C_{20}$alkyl and $R_{14}$ is H or $C_1$–$C_{20}$alkyl;
$R_{10}$ and $R_{11}$ are each independently of the other H, F, Cl or $C_1$–$C_4$alkyl, $R_{12}$ and $R_{13}$ are each independently of the other H, F, Cl, $C_1$–$C_4$alkyl, —COOH, —COO—$C_1$–$C_5$alkyl, —CONH$C_1$–$C_5$alkyl or —CON($R_{14}$)$C_1$–$C_5$alkyl, or $R_{12}$ is H and $R_{13}$ is —CN, phenyl, chlorophenyl, $C_1$–$C_{12}$alkoxy or $C_2$–$C_{18}$acyloxy.

$R_7$ is especially H or methyl and $R_8$ is especially H. X is especially —O—. $R_9$ is especially $C_6$–$C_{18}$alkyl. Examples of $R_9$ are hexyl, heptyl, octyl, 2-ethylhexyl, nonyl, decyl, dodecyl, tetradecyl, hexadecyl and octadecyl.

$R_{10}$ is especially H or methyl, $R_1$ is especially H and $R_{12}$ is especially H. $R_{13}$ is especially —CN, phenyl, —COO—$C_1$–$C_4$alkyl, $C_1$–$C_4$alkoxy or $C_2$–$C_6$acyloxy. Examples of acyloxy include acetyloxy, propionyloxy, butyroyloxy, pentanoyloxy and hexanoyloxy.

The invention relates also to a material comprising (a) a support and (b) a hydrophilic polymer, ionophore and fluorophore, wherein the active layer comprises an effective amount of a fluoroionophore of formula (I).

The support is preferably transparent and may be formed, for example, from a plastics material, such as, for example, polycarbonate or acrylic glass, mineral materials or glass and may be of any shape, for example in the form of plates, cylinders, tubes, strips or fibres. The support material may be hard or flexible. Glasses are preferred.

The thickness of the layer on the support may be, for example, from 0.01 to 100 $\mu$m, especially from 0.1 to 50 $\mu$m, especially from 0.1 to 30 $\mu$m and more especially from 0.1 to 10 $\mu$m.

Such layers may be prepared in a manner known per se, for example by dissolving the composition and, if desired, a homo- and/or co-polymer in a solvent, then casting to form a film and subsequently removing the solvent. After removal of the solvent the film can be released from the substrate and a free-standing membrane is obtained.

Other processes that may be used for the production of the membrane are those known from surface-coating technology, for example spin-coating, spraying or knife application methods. Spin-casting processes are preferred.

Suitable solvents include water, alcohols, ethers, esters, acid amides and ketones. Readily volatile solvents, especially tetrahydrofuran, or solvent mixtures are especially suitable.

The membrane may be transparent or slightly opaque. It is preferably transparent. The layer is preferably hydrophilic.

The invention relates also to an optical sensor comprising a support coated on at least one side with a hydrophilic polymer, ionophore and fluorophore, wherein the active layer comprises an effective amount of a fluoroionophore of formula (I).

The optical range in which the material as sensor can be excited extends from the ultra-violet range to the infrared range. The immobilised fluorophoreionophores to be used in accordance with the invention have very suitable absorption and emission wavelength ranges that allow the use of known economically priced, low-energy light sources, for example halogen or xenon lamps or light-emitting diodes. The preferred excitation source is a light-emitting diode having a wavelength of 400 nm or above. The detectors used to detect the fluorescence may be, for example, photodiodes. Commercially obtainable optical fibres may be used in the excitation and detection. The sensor may therefore be changed after use on a patient.

The optical sensor is suitable especially for the quantitative determination of sodium ions, in an aqueous environment preferably using fluorescence spectrometry. The determinations may be effected within short periods of time with a high degree of accuracy even in the case of low concentrations (for example extending from the millimolar range to the nanomolar range).

A very important advantage of the immobilised fluoroionophores is that they offer the possibility of carrying out measurements that are substantially independent of pH value. There is a much freer choice of fluoroionophores since proton exchange at the fluorophore is not necessary for the detection of ions. In addition, direct measurement of the solution to be analysed is possible, which is of considerable commercial advantage. If desired, however, it is also possible in some cases for the measurements to be carried out in buffered analysis solutions when, for example, fluorophores are used that result in signal change as a result of proton exchange.

The analyses may be carried out, for example, directly in body fluids (blood, urine, serum), natural waters or waste water, it being possible for cations that may interfere to be selectively bonded or removed beforehand. The composition according to the invention is suitable especially for determining in aqueous media physiological amounts of sodium which may be, for example, in the range from 50 mmol to 200 mmol.

In addition to the preferred fluorescence spectroscopy, other methods of optical measurement may also be used, for example surface plasmon resonance spectroscopy, absorption spectroscopy, reflection spectroscopy, interferometry or surface-enhanced Raman or fluorescence spectroscopy.

The invention relates also to a method for the optical determination of sodium ions in aqueous test samples, in which method a sensor according to the invention is brought into contact with the said aqueous test sample and then the change in the fluorescence of the fluorophore in the polymer layer is measured.

The method according to the invention may be carried out, for example, by fixing the support with the active polymer layer in an optical cell in which the active layer comes into contact with the test sample. The optical cell has a window through which the active layer can be irradiated for the purpose of excitation and through which the emitted fluorescence radiation can be measured using a spectrofluorometer. The wavelengths may be adjusted to provide maximum absorption for the irradiation and maximum emission for the fluorescence measurement. The intensity is measured as a function of time. The measuring system may be so arranged that the measurement is carried out discontinuously or continuously by, for example, pumping the test solution through the measuring cell. To determine unknown concentrations of sodium ions, the system may first be calibrated using test samples of known concentration by plotting the concentrations against the intensity of the fluorescence.

The invention relates also to the use of the optical sensor for the determination of sodium ions by fluorescence spectroscopy.

The following Examples illustrate the invention.

The following abbreviations are used in the Examples:
DABCO: 1,4-diazabicyclo[2.2.2]octane
DMF: dimethylformamide
MS(FD): mass spectrometry (field desorption)
abs.: absorption
em.: emission
THF: tetrahydrofuran
MS: mass spectrum
FAB: fast atom bombardment
RPM: revolutions per minute

A) Preparation of the Fluoroionophores

Example A1

Preparation of Compound A1 a)

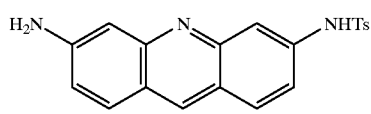
1

500 mg of 3,6-diaminoacridine are dissolved with 455 mg of tosyl chloride in 15 ml of THF with the addition of 1 ml of pyridine, and the reaction mixture is stirred for 21 hours. After concentration of the reaction mixture by evaporation, the residue is chromatographed on silica gel. Yield 110 mg (12%) monotosyl compound with ditosyl compound in addition.

b)

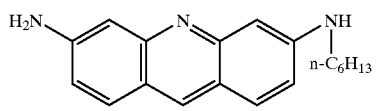
2

100 mg of Compound 1 are stirred with 50 mg of 1-bromohexane and 46 mg of potassium carbonate in 5 ml of DMF at 80° C. for 4 hours. The reaction mixture is added to water and adjusted to pH 1. Extraction is then carried out with methylene chloride, followed by drying and concentration by evaporation. The residue is chromatographed on silica gel.

Yield 61%. MS(FD): 447 c)

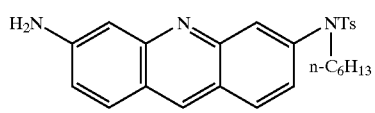
3

1.14 g of Compound 2 are stirred in 25 ml of a 2:5 mixture of sulfuric acid and acetic acid at room temperature for 22 hours. The reaction mixture is then poured onto 500 ml of 2N NaOH, and extraction is carried out with ethyl acetate. After concentration of the organic phase by evaporation, the residue is reprecipitated from methylene chloride/hexane. Yield 93%. $\lambda_{max.}$(absorption; c=1.3 mg/50 ml EtOH): 466 nm. $\lambda_{max.}$(emission; c=1.3 mg/50 ml EtOH)=490 nm.

d)

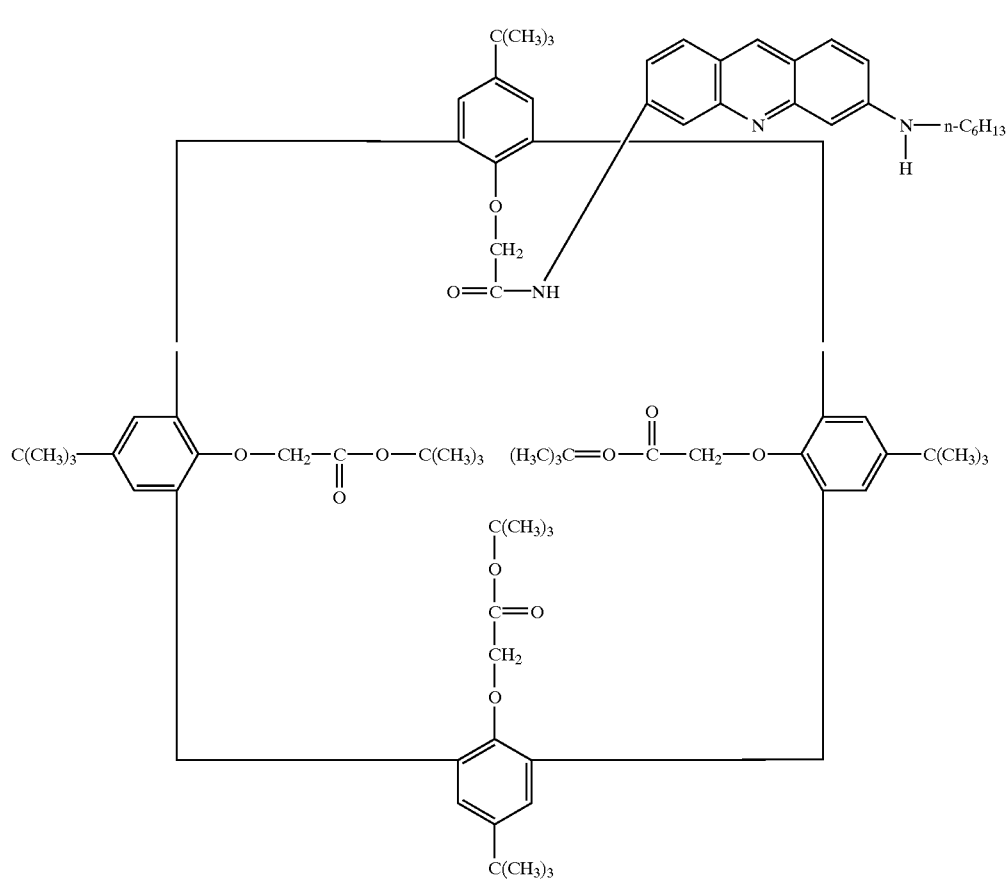
A1

25-Carboxylic acid-26,27,28-tri-tert-butylester-p-tenbutylcalix[4]arene [1] (50 mg) is placed in 2.5 ml of THF, and 60 mg of oxalyl chloride are added. After 3 hours at room temperature, concentration by evaporation and drying under a high vacuum are carried out. The residue is dissolved in 2.5 ml of THF, and 14 mg of Compound 3 and 14 mg of potassium carbonate are added. After stirring overnight, concentration by evaporation and drying under a high vacuum are carried out. Purification is carried out by chromatography on silica gel. Yield 40%. MS (FAB):1325 (M+D)$^+$; 1347 (M+Na)$^+$. $\lambda_{max}$.(absorption EtOH): 435 nm; $\lambda_{max}$.(emission EtOH): 511 nm.

EXAMPLE A2

Preparation of Compound A2

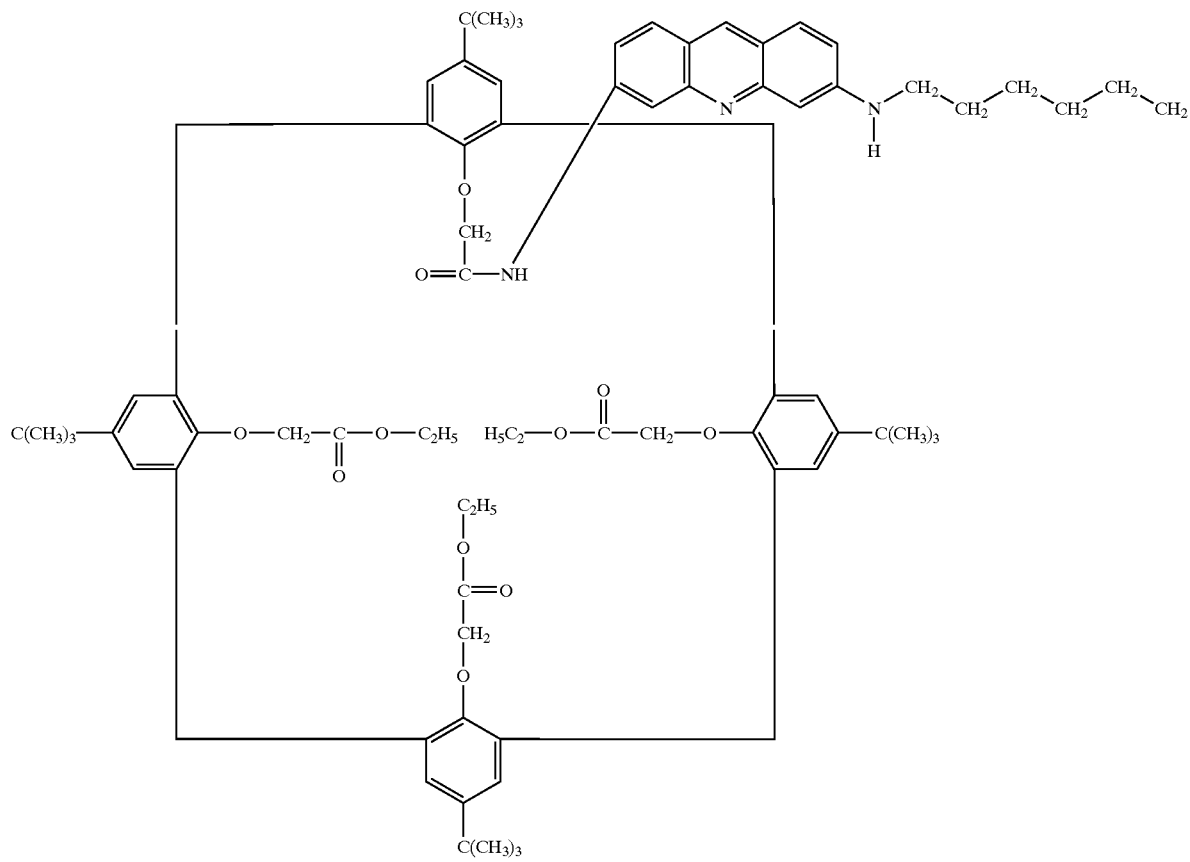

A2

Calixarenecarboxylic acid triethyl ester (0.52 mmol) is refluxed in 2 ml of thionyl chloride for 2.5 hours. Excess thionyl chloride is distilled off and the residue is dried under a high vacuum. The acid chloride is dissolved in 15 ml of methylene chloride, and one molar equivalent of each of triethylamine and N(3)-n-hexyl-3,6-diaminoacridine is added. After being stirred at room temperature overnight, the reaction mixture is diluted with methylene chloride and washed with 5% acetic acid. The organic phase is washed with saturated hydrogen carbonate solution, dried and concentrated by evaporation. Purification of the residue is carried out by chromatography on silica gel using methylene chloride/methanol 100:0 to 1:1. FAB-MS: 1240 [M+H]$^+$; 1262 [M+Na]$^+$.

B) Preparation of the Polymers

EXAMPLE B1

Preparation of Polyurethane BEC 45

4.27 g (4.5 mmol) of polyethylene glycol (PEG) (molecular weight: 948 (Siegfried)) are dissolved in 40 ml of tetrahydrofuran (THF), and 0.18 g (2.0 mmol) of butanediol (BDO) and 13 mg of DABCO are added. At 60° C., 1.63 g (6.5 mmol) of methylenediphenyl diisocyanate (MDI) are added. After 30 minutes, a further 0.2 g (0.8 mmol) of MDI, dissolved in 3 ml of THF, is added in portions. After 16 hours, 1 ml (11 mmol) of BDO is added. After a further 2 hours, the viscous solution is poured into 1000 ml of methanol. The tacky polymer is separates out. After decanting, the polymer is dried (16 hours at room temperature/100 mbar and 8 hours at room temperature/2 mbar).

Crude yield: 3.97 g (63%)
OH terminal groups: 0.23 molar equivalenvg
Glass transition temperature=–27° C.
Inherent viscosity $\eta_{inh}$=0.246 dl/g (0.5% solution in THF at 25° C.).

C) Production of Sensors

EXAMPLE C1

Production of a Sensor Using an Acrylate Polymer 0.5 mg of the fluoroionophore A1 and 145 mg of poly(hydroxybutyl acrylate) [Scientific Polymer Products, Ontario N.Y. USA catalogue number 888] are dissolved in 0.5 ml of isopropanol. 100 µl of the above solution are applied (spin-coating) to a glass substrate having a diameter of 18 mm at a speed of 5000 RPM. The glass substrate is then dried at room temperature overnight.

Solutions of different concentrations are pumped through a flow cell containing the sensor. The following Table lists the signal as a function of various sodium concentrations.

| Sodium concentration (mmol/litre) | Fluorescence intensity (V) |
|---|---|
| 0 | 0.23 |
| 10 | 0.24 |
| 50 | 0.25 |
| 100 | 0.26 |
| 300 | 0.32 |
| 500 | 0.45 |
| 700 | 0.65 |
| 1000 | 0.95 |

EXAMPLE C2
Sensor Using a Polyurethane Polymer 10 mg of the fluoroionophore A1 and 150 mg of polyurethane (BEC 45) are dissolved in tetrahydrofuran.

100 μl of the above solution are applied (spin-coating) to a glass substrate having a diameter of 18 mm at a speed of 5000 RPM. The glass substrate is then dried at room temperature overnight.

Solutions of different concentrations are pumped through a flow cell containing the sensor. The following Table lists the signal as a function of various sodium concentrations.

| Sodium concentration (mmol/litre) | Fluorescence intensity (V) |
|---|---|
| 0 | 0.158 |
| 50 | 0.180 |
| 300 | 0.290 |
| 1000 | 0.360 |

D) Application Example
Ion Detection Using the Sensors

Apparatus:

The test apparatus is a conventional fluorescence apparatus. The light beam of a tungsten halogen lamp is used as excitation source and is focused by various lens and filter systems (including a dichroic filter that is set at 450) onto the sensor surface fixed in a flow cell. The emitted light is focused onto a photodiode detector and the fluorescence intensity is recorded in volts by a computer.

What is claimed is:

1. A composition comprising a polymer which is permeable to ions and a fluoroionophore of formula (I)

(I)

wherein
   $R_{06}$ is H or $C_1$–$C_{20}$alkyl,
   $R_6$ is $C_1$–$C_{30}$alkyl or $C_1$–$C_{30}$alkoxy,
   $R_1$ is a bridging group which
   (a) corresponds to formula (II)

$$-X_1-(R_3)_r-X_2-$$  (II)

wherein $X_1$ is —$NR_5$—,
   $X_2$ is a direct bond or is selected from the group consisting of —O—, —S—, —$NR_5$—, —C(O)—O—, —O—C(O)—, —O—C(O)—O—, —$SO_2$—O—, —O—$SO_2$—, —O—$SO_2$—O—, —$NR_5$—C(O)—, —C(O)—$NR_5$—, —$NR_5$—C(O)—O—, —O—C(O)—$NR_5$—, —$NR_5$—C(O)—$NR_5$—, —$NR_5SO_2$—, —$SO_2$—$NR_5$—, —$NR_5$—$SO_2$—O—, —O—$SO_2NR_5$— and
   $NR_5SO_2$—$NR_5$—,
   $R_5$ is H or $C_1$–$C_{30}$alkyl, $C_5$- or $C_6$-cycloalkyl, $C_5$- or $C_6$-cycloalkylmethyl or -ethyl, phenyl, benzyl or 1-phenyleth-2-yl,
   $R_3$ is a carbon-containing divalent bridging group, and
   r is 0 or 1, with the proviso that r is 1 when $X_2$ is one of the mentioned groups, or
   (b) corresponds to formula (II)

$$-X_1-(R_3)_r-X_2-$$  (II)

wherein $X_1$ is —O—,
   $X_2$ is selected from the group consisting of —O—, —S—, —$NR_5$—, —C(O)—O—, —O—C(O)—, —O—C(O)—O—, —$SO_2$—O—, —O—$SO_2$—, —O—$SO_2$—O—, —$NR_5$—C(O)—, —C(O)—$NR_5$—, —$NR_5$—C(O)—O—, —O—C(O)—$NR_5$—, —$NR_5$—C(O)—$NR_5$—, —$NR_5SO_2$—, —$SO_2$—$NR_5$—, —$NR_5$—$SO_2$—O—, —O—$SO_2NR_5$— and
   —$NR_5SO_2$—$NR_5$—,
   $R_5$ is H or $C_1$–$C_{30}$alkyl, $C_5$- or $C_6$-cycloalkyl, $C_5$- or $C_6$-cycloalkylmethyl or -ethyl, phenyl, benzyl or 1-phenyleth-2-yl,
   $R_3$ is a carbon-containing divalent bridging group, and
   r is 1, and
   F is a residue of a fluorophore selected from the group consisting of a fluorescein, derivatives of a fluorescein, a rhodamine, derivatives of a rhodamine, an acridine, derivatives of an acridine, and a fluorophore composed of condensed ring systems selected from the group consisting of naphthalenes, benzofurans, benzodiazines, benzotrioxazines and benzotriazepines.

2. A composition according to claim 1, wherein $R_6$ is linear or branched $C_1$–$C_{10}$alkyl.

3. A composition according to claim 1, wherein $R_6$ is linear or branched $C_1$–$C_4$alkyl.

4. A composition according to claim 3, wherein $R_6$ is tertiary butyl.

5. A composition according to claim 1, wherein $R_{06}$ is linear or branched $C_1$–$C_{10}$alkyl.

6. A composition according to claim 1, wherein $R_{06}$ is H or linear or branched $C_1$–$C_4$alkyl.

7. A composition according to claim 6, wherein $R_{06}$ is tertiary butyl or ethyl.

8. A composition according to claim 1, wherein the bridging group $R_1$ corresponds to formula (II)

$$-X_1-(R_3)_r-X_2-$$  (II)

wherein $X_1$ is —O— or —$NR_5$,
   $X_2$ is a direct bond or is selected from the group consisting of —O—, —S—, —$NR_5$—, —C(O)—O—, —O—C(O)—, —O—C(O)—O—, —SO$_2$—O—, —O—SO$_2$—, —O—SO$_2$—O—, —NR$_5$—C(O)—, —C(O)—NR$_5$—, —NR$_5$—C(O)—O—, —O—C(O)—NR$_5$—, —NR$_5$—C(O)—NR$_5$—, —NR$_5$SO$_2$—, —SO$_2$—NR$_5$—, —NR$_5$—SO$_2$—O—, —O—SO$_2$NR$_5$— and —NR$_5$SO$_2$—NR$_5$—, R$_5$ is H or C$_1$–C$_{30}$alkyl, C$_5$- or C$_6$-cycloalkyl, C$_5$- or C$_6$-cycloalkylmethyl or -ethyl, phenyl, benzyl or 1-phenyleth-2-yl, R$_3$ is a divalent bridging group which is a hydrocarbon radical that contains from 1 to 30 carbon atoms and that is unsubstituted or mono- or poly-substituted by C$_1$–C$_4$alkyl, C$_1$–C$_4$alkoxy or by =O, and r is 0 or 1, with the proviso that r is 1 when X$_2$ is one of the mentioned groups.

9. A composition according to claim 8, wherein the hydrocarbon radical is interrupted one or more times by hetero atoms selected from the group consisting of —O—, —S— and —NR$_5$— wherein R$_5$ is H or C$_1$–C$_4$alkyl.

10. A composition according to claim 1, wherein the fluorophore from which F in formula (I) is derived is a fluorescein or a derivative thereof.

11. A composition according to claim 1, wherein the fluorophore from which F in formula (I) is derived is a rhodamine or a derivative thereof.

12. A composition according to claim 1, wherein the fluorophore from which F in formula (I) is derived is an acridine or a derivative thereof.

13. A composition according to claim 1, wherein the fluorophore from which F in formula (I) is derived is a 3,6-diaminoacridine.

14. A composition according to claim 1, wherein the fluorophore from which F in formula (I) is derived is an acridine of formula (V)

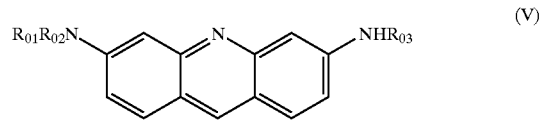

wherein R$_{01}$ and R$_{02}$ are each independently of the other H or linear or branched C$_1$–C$_{30}$-alkyl and R$_{03}$ is H or C$_1$–C$_6$alkyl.

15. A composition according to claim 1, wherein the fluoroionophore is a compound of formula (Ia)

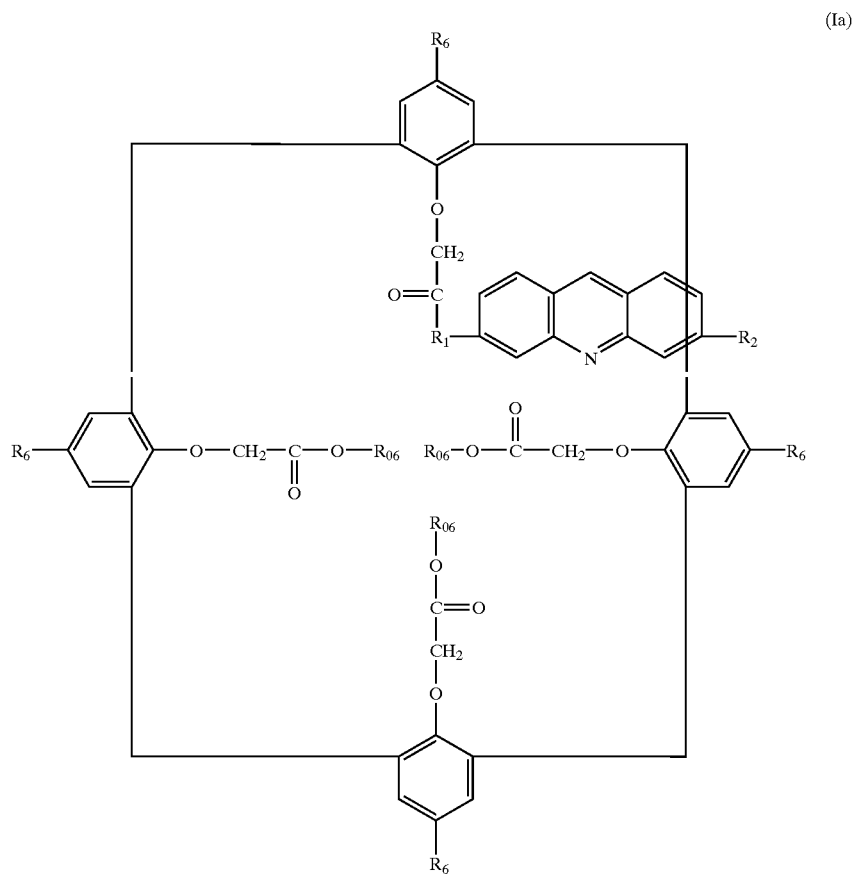

wherein R$_2$ is —NR$_{01}$R$_{02}$ wherein R$_{01}$ and R$_{02}$ are each independently of the other H or linear or branched C$_1$–C$_{30}$-alkyl.

16. A composition according to claim 15, wherein R$_6$ is linear or branched C$_1$–C$_{10}$alkyl.

17. A composition according to claim 15, wherein R$_6$ is linear or branched C$_1$–C$_4$alkyl.

18. A composition according to claim 15, wherein R$_6$ is tertiary butyl.

19. A composition according to claim 15, wherein R$_{06}$ is linear or branched C$_1$–C$_{10}$alkyl.

20. A composition according to claim 15, wherein $R_{06}$ is linear or branched $C_1$–$C_4$alkyl.

21. A composition according to claim 15, wherein $R_{06}$ is tertiary butyl or ethyl.

22. A composition according to claim 15, wherein $R_2$ is —$NR_{01}R_{02}$ wherein $R_{01}$ and $R_{02}$ are each independently of the other H or linear or branched $C_1$–$C_{10}$.

23. A composition according to claim 1, wherein the fluoroionophore is a compound of formula (Ia)

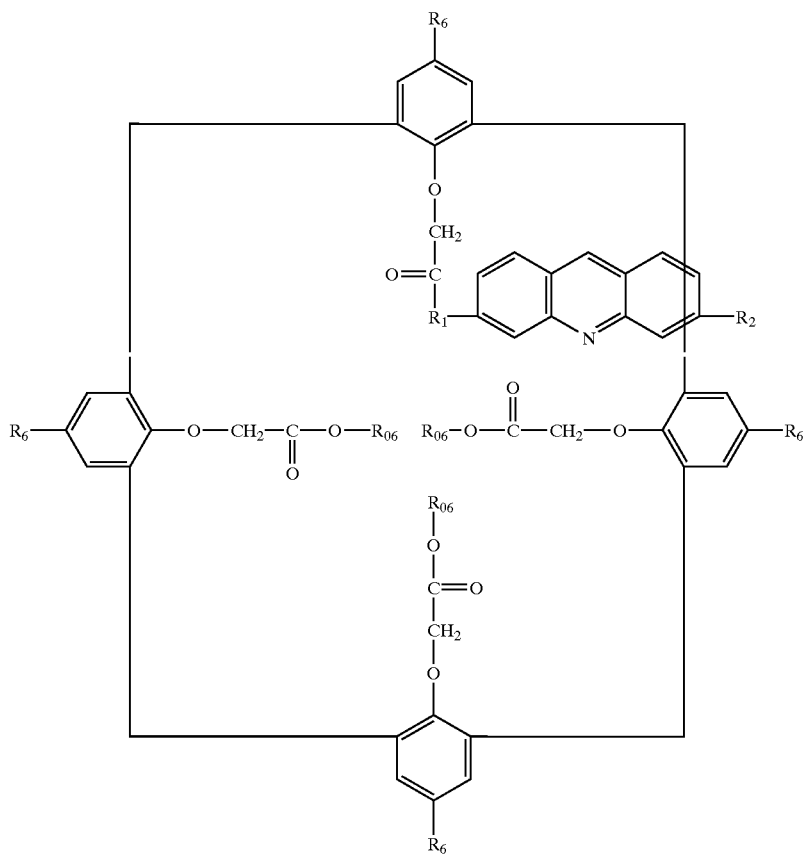

wherein $R_2$ is —$NR_{01}R_{02}$ wherein $R_{01}$ and $R_{02}$ are each independently of the other H or linear or branched $C_1C_{30}$-alkyl, the minimum carbon atom content of $R_{01}$ and $R_{02}$ being at least 20.

24. A composition according to claim 15, wherein the bridging group $R_1$ corresponds to formula (II)

$$-X_1-(R_3)_r-X_2- \qquad (II)$$

wherein $X_1$ is —O— or —$NR_5$, $X_2$ is a direct bond and r is 0.

25. A composition according to claim 24, wherein $X_1$ is NH.

26. A composition according to claim 1, wherein the fluoroionophore corresponds to the formula

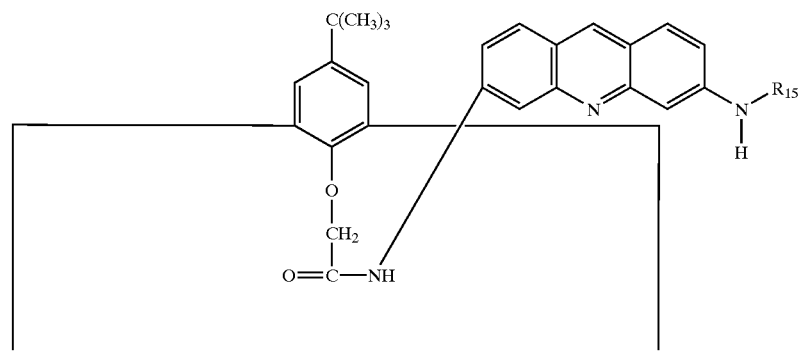

-continued

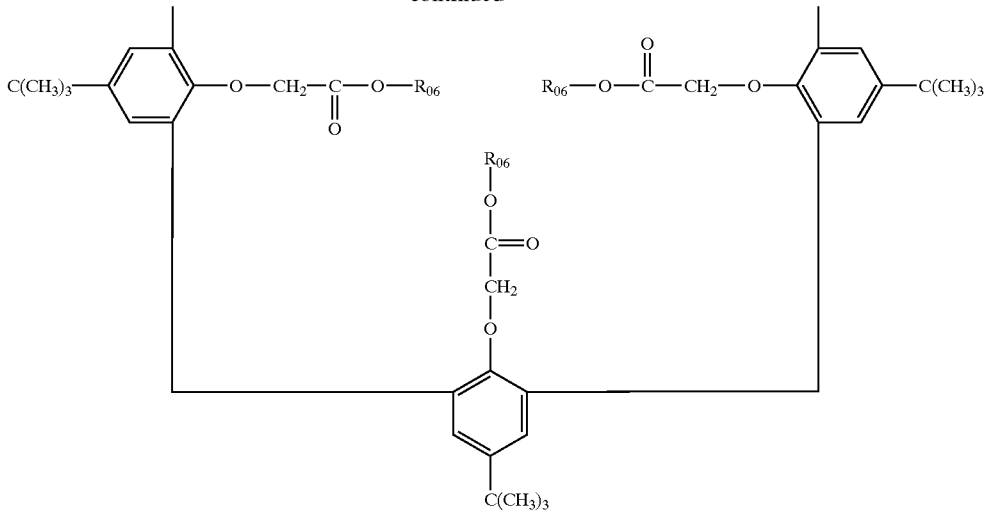

wherein $R_{15}$ is $C_1$–$C_{20}$alkyl.

27. A composition according to claim 1, wherein the polymer has a molecular weight of at least 5000 daltons.

28. A composition according to claim 1, wherein the polymer is selected from the group consisting of polyvinyl compounds and polyacrylates, polyesters, polyamides, polyethers, polyimides, polyester amides, polyamide imides, polyurethanes, polyether urethanes, polyester urethanes, polyureas, polyurethane ureas and polysiloxanes.

29. A composition according to claim 1, wherein the polymer comprises ionisable basic or acidic groups.

30. A composition according to claim 28, wherein the polymer is a polyurethane of a polyether of a $C_3$–$C_6$alkanediol and an aliphatic, cycloaliphatic, cycloaliphatic-aliphatic, aromatic-aliphatic or aromatic $C_2$–$C_{20}$diisocyanate.

31. A composition according to claim 28, wherein the polymer is a copolymer having from 10 to 90 mol % of identical or different structural units of formula III

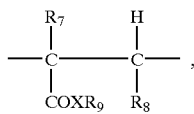

(III)

and from 90 to 10 mol %, based on the polymer, of identical or different structural units of formula IV

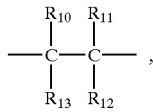

(IV)

wherein $R_7$ and $R_8$ are each independently of the other H or $C_1$–$C_4$alkyl, X is —O— or
—$NR_{14}$—, $R_9$ is $C_6$–$C_{20}$alkyl and $R_{14}$ is H or $C_1$–$C_{20}$alkyl;
$R_{10}$ and $R_{11}$ are each independently of the other H, F, Cl or $C_1$–$C_4$alkyl, $R_{12}$ and $R_{13}$ are each independently of the other H, F, Cl, $C_1$–$C_4$alkyl, —COOH, —COO—$C_1$–$C_5$alkyl,
—CONH$C_1$–$C_5$alkyl or —CON($R_{14}$)$C_1$–$C_5$alkyl, or $R_{12}$ is H and $R_{13}$ is —CN, phenyl, chlorophenyl, $C_1$–$C_{12}$alkoxy or $C_2$–$C_{18}$acyloxy.

32. A material comprising (a) a support and (b) an active layer thereon, wherein the active layer comprises a hydrophilic polymer which is permeable to ions and an effective amount of a fluoroionophore of formula (I)

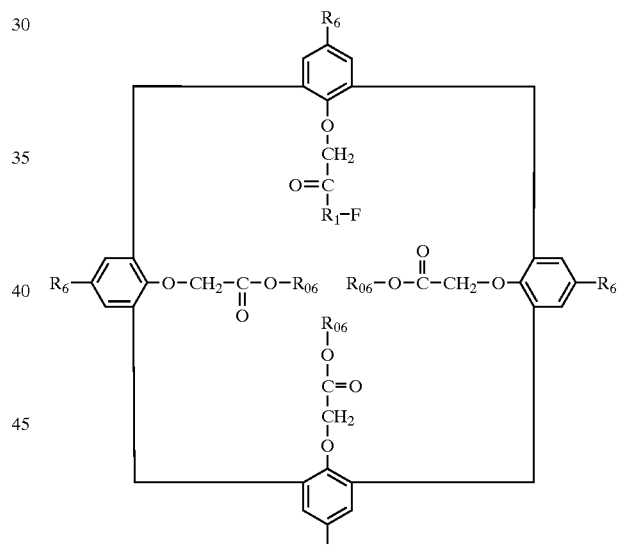

(I)

wherein
$R_{06}$ is H or $C_1$–$C_{20}$alkyl,
$R_6$ is $C_1$–$C_{30}$alkyl or $C_1$–$C_{30}$alkoxy,
$R_1$ is a bridging group which
(a) corresponds to formula (II)

$$—X_1—(R_3)_r—X_2—$$ (II)

wherein $X_1$ is —$NR_5$—,
$X_2$ is a direct bond or is selected from the group consisting of —O—, —S—, —$NR_5$—, —C(O)—O—, —O—C(O)—, —O—C(O)—O—, —$SO_2$—O—, —O—$SO_2$—, —O—$SO_2$—O—, —$NR_5$—C(O)—, —C(O)—$NR_5$—, —$NR_5$—C(O)—O—, —O—C(O)—$NR_5$—, —$NR_5$—C(O)—$NR_5$—, —$NR_5SO_2$—, —$SO_2$—$NR_5$—, —$NR_5$—$SO_2$—O—, —O—$SO_2NR_5$— and —$NR_5SO_2$—$NR_5$—, $R_5$ is H or $C_1$–$C_{30}$alkyl, $C_5$- or $C_6$-cycloalkyl, $C_5$- or $C_6$-cycloalkylmethyl or -ethyl, phenyl, benzyl or 1-phenyleth-2-yl, $R_3$ is a carbon-containing divalent bridging group, and r is 0 or 1, with the proviso that r is 1 when $X_2$ is one of the mentioned groups, or (b) corresponds to formula (II)

  (II)

wherein $X_1$ is —O—, $X_2$ is selected from the group consisting of —O—, —S—, —$NR_5$—, —C(O)—O—,
—O—C(O)—, —O—C(O)—O—, —$SO_2$—O—,
—O—$SO_2$—, —O—$SO_2$—O—, —$NR_5$—C(O)—,
—C(O)—$NR_5$—, —$NR_5$—C(O)—O—,
—O—C(O)—$NR_5$—, —$NR_5$—C(O)—$NR_5$—,
—$NR_5SO_2$—, —$SO_2$—$NR_5$—, —$NR_5$—$SO_2$—O—,
—O—$SO_2NR_5$— and
—$NR_5SO_2$—$N_5$—, $R_5$ is H or $C_1$–$C_{30}$alkyl, $C_5$- or $C_6$-cycloalkyl, $C_5$- or $C_6$-cycloalkylmethyl or -ethyl, phenyl, benzyl or 1-phenyleth-2-yl, $R_3$ is a carbon-containing divalent bridging group, and r is 1, and F is a residue of a fluorophore selected from the group consisting of a fluorescein, derivatives of a fluorescein, a rhodamine, derivatives of a rhodamine, an acridine, derivatives of an acridine, and a fluorophore composed of condensed ring systems selected from the group consisting of naphthalenes, benzofurans, benzodiazines, benzotrioxazines and benzotriazepines.

33. A material according to claim 32, wherein the support is transparent.

34. A material according to claim 32, wherein the thickness of the layer on the support is from 0.01 to 100 μm.

35. A method for the optical determination of sodium ions in aqueous test samples, wherein an active layer of a material according to claim 32 is brought into contact with an aqueous test sample and then the change in increasing fluorescence is measured.

* * * * *